(12) United States Patent
Shibutani et al.

(10) Patent No.: US 6,623,117 B2
(45) Date of Patent: Sep. 23, 2003

(54) EYE'S OPTICAL CHARACTERISTIC MEASURING SYSTEM

(75) Inventors: Masahiro Shibutani, Tokyo-to (JP); Katsuhiko Kobayashi, Tokyo-to (JP); Gaku Takeuchi, Tokyo-to (JP)

(73) Assignee: Kabushiki Kaisha TOPCON, Tokyo-to (JP)

( * ) Notice: Subject to any disclaimer, the term of this patent is extended or adjusted under 35 U.S.C. 154(b) by 0 days.

(21) Appl. No.: 10/037,379

(22) Filed: Nov. 7, 2001

(65) Prior Publication Data

US 2002/0063851 A1 May 30, 2002

(30) Foreign Application Priority Data

Nov. 30, 2000 (JP) ........................................ 2000-364834

(51) Int. Cl.[7] ................................................. A61B 3/10
(52) U.S. Cl. ..................................................... 351/211
(58) Field of Search ................................ 351/200, 211, 351/212, 221; 356/124

(56) References Cited

U.S. PATENT DOCUMENTS 6,271,914 B1 * 8/2001 Frey et al. .................. 356/124
6,299,311 B1 * 10/2001 Williams et al. ............. 351/221
6,315,412 B1 * 11/2001 Snodderly et al. .......... 351/200

* cited by examiner

Primary Examiner—George Manuel
(74) Attorney, Agent, or Firm—Nields & Lemack

(57) ABSTRACT

An eye's optical characteristic measuring system, comprising an index projection system 2 for projecting an index image on a fundus of an eye under testing, a photodetection optical system 3 for guiding the index image toward a photoelectric detector, a simulation image calculating unit 28 for calculating each of images of target images formed when a plurality of target images different in size are respectively projected on the fundus of the eye under testing based on a light amount intensity distribution of the index image detected on the photoelectric detector, and a visual acuity calculating unit 28 for calculating a visual acuity value of the eye under testing, wherein the simulation image calculating unit calculates light amount intensity distributions in each of predetermined meridian directions of the images of the target images, and the visual acuity calculating unit detects a plurality of light amount intensity distribution values based on the light amount intensity distributions and calculates the visual acuity value of the eye under testing based on the plurality of light amount intensity distribution values.

11 Claims, 9 Drawing Sheets

$Ixy = Oxy * Pxy$

FUNDUS SIMULATION ··· Landolt Chart ···
FIG. 8A
FIG. 8B
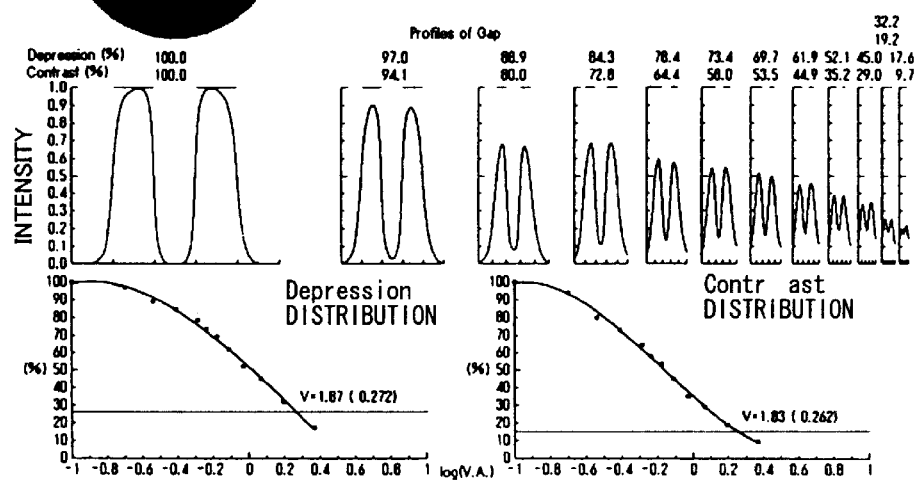
FIG. 8C

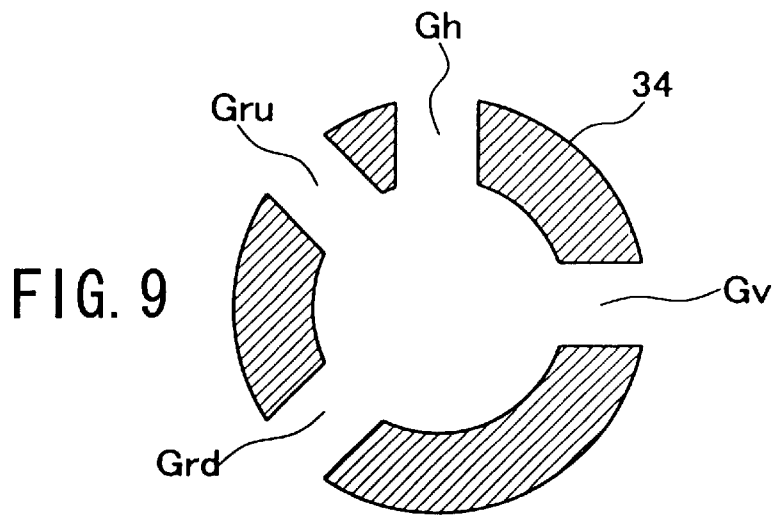
FIG. 9
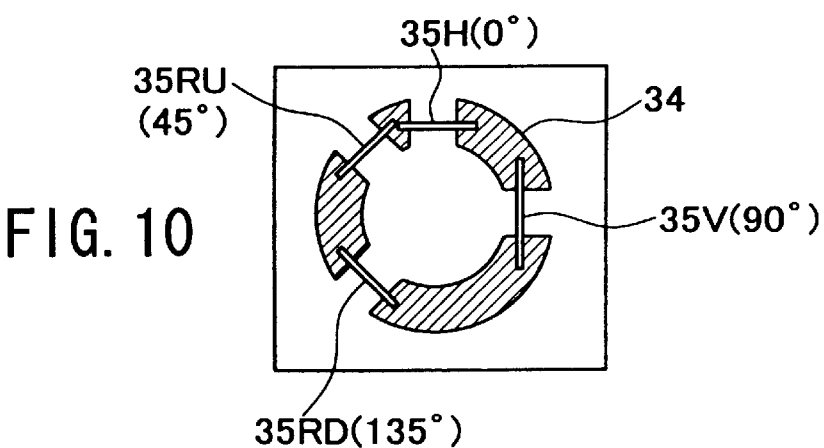
FIG. 10
FIG. 11
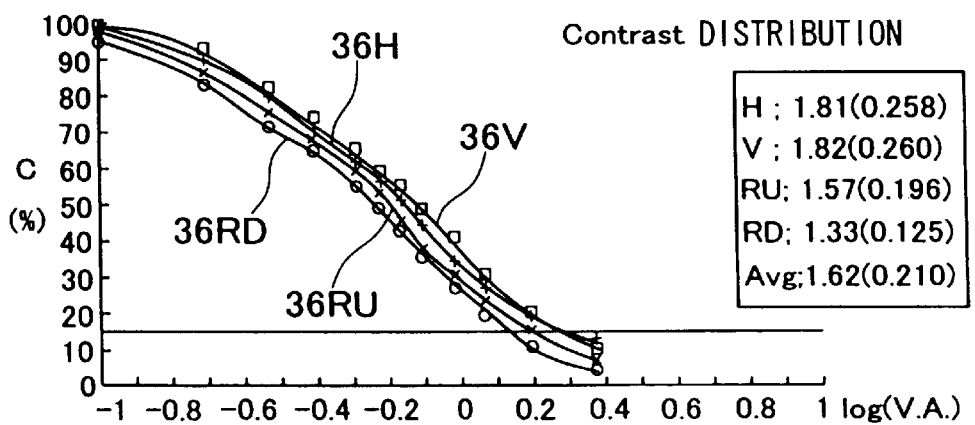

REFLECTION

SCATTERING

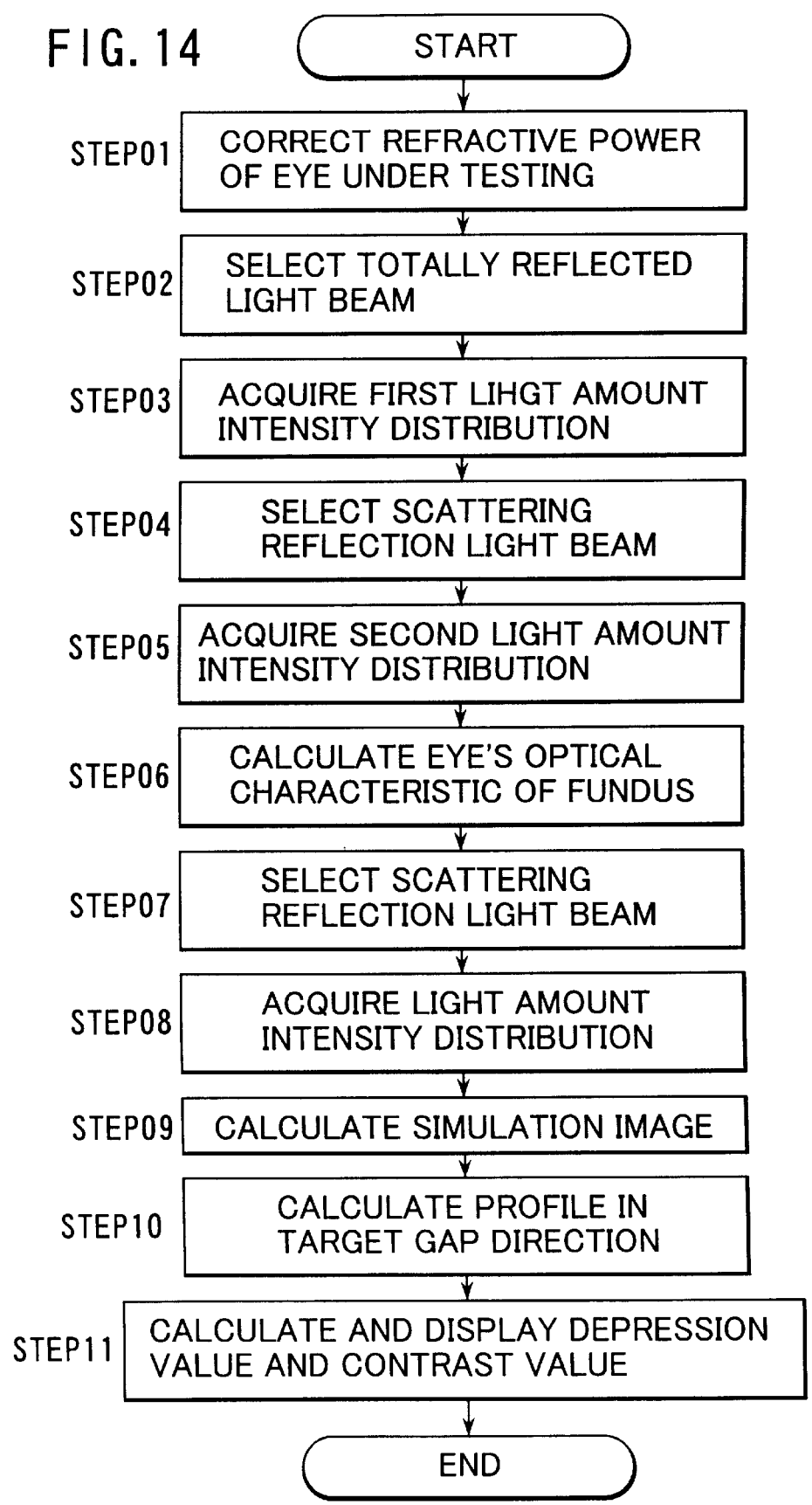

000
EYE'S OPTICAL CHARACTERISTIC MEASURING SYSTEM

BACKGROUND OF THE INVENTION

The present invention relates to an eye's optical characteristic measuring system, by which it is possible to estimate and calculate a visual acuity of an eye under testing based on a light amount intensity distribution characteristic of an index image projected on a fundus of the eye under testing.

In the past, the present applicant has already filed a patent application on a system, which comprises a target projection system for projecting an index image to a fundus of an eye under testing and a photodetection optical system for guiding the index image toward a photoelectric detector, in which a simulation image on the fundus of the eye is calculated, which may be formed when the target image is projected on the fundus of the eye under testing, based on a light amount intensity distribution of the index image detected at the photoelectric detector. By this system, based on a result of the calculation, it is possible to detect which kind of image is formed on the fundus of the eye under testing.

In this system, it is possible to calculate under which condition various kinds of the target images are projected to the fundus of the eye under testing without actually projecting various kinds of the target images.

However, in the system proposed in the above patent application, it is advantageous in that the image itself obtained by simulation can be observed, while, with respect to the visual acuity value of the eye under testing, the tester must estimate the visual acuity value from the result of the observation. In this respect, there has been a problem in that it is difficult to obtain the accurate visual acuity value.

SUMMARY OF THE INVENTION

It is an object of the present invention to provide an eye's optical characteristic measuring system, by which it is possible to solve the problem of the conventional type eye's optical characteristic measuring system and to obtain an objectively accurate visual acuity value from the measured data without asking the person under testing about the result of visual observation.

To attain the above object, the eye's optical characteristic measuring system according to the present invention comprises an index projection system for projecting an index image on a fundus of an eye under testing, a photodetection optical system for guiding the index image toward a photoelectric detector, a simulation image calculating unit for calculating each of images of target images formed when a plurality of target images different in size are respectively projected on the fundus of the eye under testing based on a light amount intensity distribution of the index image detected on the photoelectric detector, and a visual acuity calculating unit for calculating a visual acuity value of the eye under testing, wherein the simulation image calculating unit calculates light amount intensity distributions in each of predetermined meridian directions of the images of the target images, and the visual acuity calculating unit detects a plurality of light amount intensity distribution values based on the light amount intensity distributions and calculates the visual acuity value of the eye under testing based on the plurality of light amount intensity distribution values. Further, the present invention provides the eye's optical characteristic measuring system as described above, wherein the light amount intensity distribution characteristic value is detected based on each light amount distribution in a plurality of the predetermined meridian directions of the image of the each target image, and the visual acuity value of the eye under testing is calculated based on the values of light amount intensity distribution characteristic in the plurality of the predetermined meridian directions. Also, the present invention provides the eye's optical characteristic measuring system as described above, wherein the visual acuity value of the eye under testing is calculated from an average value of the light amount intensity distribution characteristic values obtained in each of the predetermined meridian directions. Further, the present invention provides the eye's optical characteristic measuring system as described above, wherein a light amount intensity distribution characteristic value-visual acuity curve is obtained by interpolating a plurality of light amount intensity distribution characteristic values in the predetermined meridian direction and the visual acuity value of the eye under testing is calculated based on the light amount intensity distribution characteristic value-visual acuity curve. Also, the present invention provides the eye's optical characteristic measuring system as described above, wherein the light amount intensity distribution characteristic value of the image of the target image is a contrast value. Further, the present invention provides the eye's optical characteristic measuring system as described above, wherein the light amount intensity distribution characteristic value of the image of the target image is a depression value. Also, the present invention provides the eye's optical characteristic measuring system as described above, wherein at least one gap is formed in the target image, and the predetermined meridian direction is a direction to traverse the gap of the image of the target image.

BRIEF DESCRIPTION OF THE DRAWINGS

FIG. 3 represents diagrams showing a light amount intensity distribution obtained in the measurement of the embodiment of the present invention.

FIG. 8 shows an example of a display when a simulation image, a profile, a depression value—visual acuity curve, and a contrast value—visual acuity curve are displayed on the same screen;

FIG. 9 shows an example of a target having a plurality of gaps;

FIG. 10 is a drawing to explain the above target and the target gap directions;

FIG. 11 is a diagram showing a contrast value-visual acuity curve obtained by the target having a plurality of gaps;

FIG. 14 is a flow chart of measurement in another embodiment of the present invention.

DETAILED DESCRIPTION OF THE PREFERRED EMBODIMENT

Figure 1:
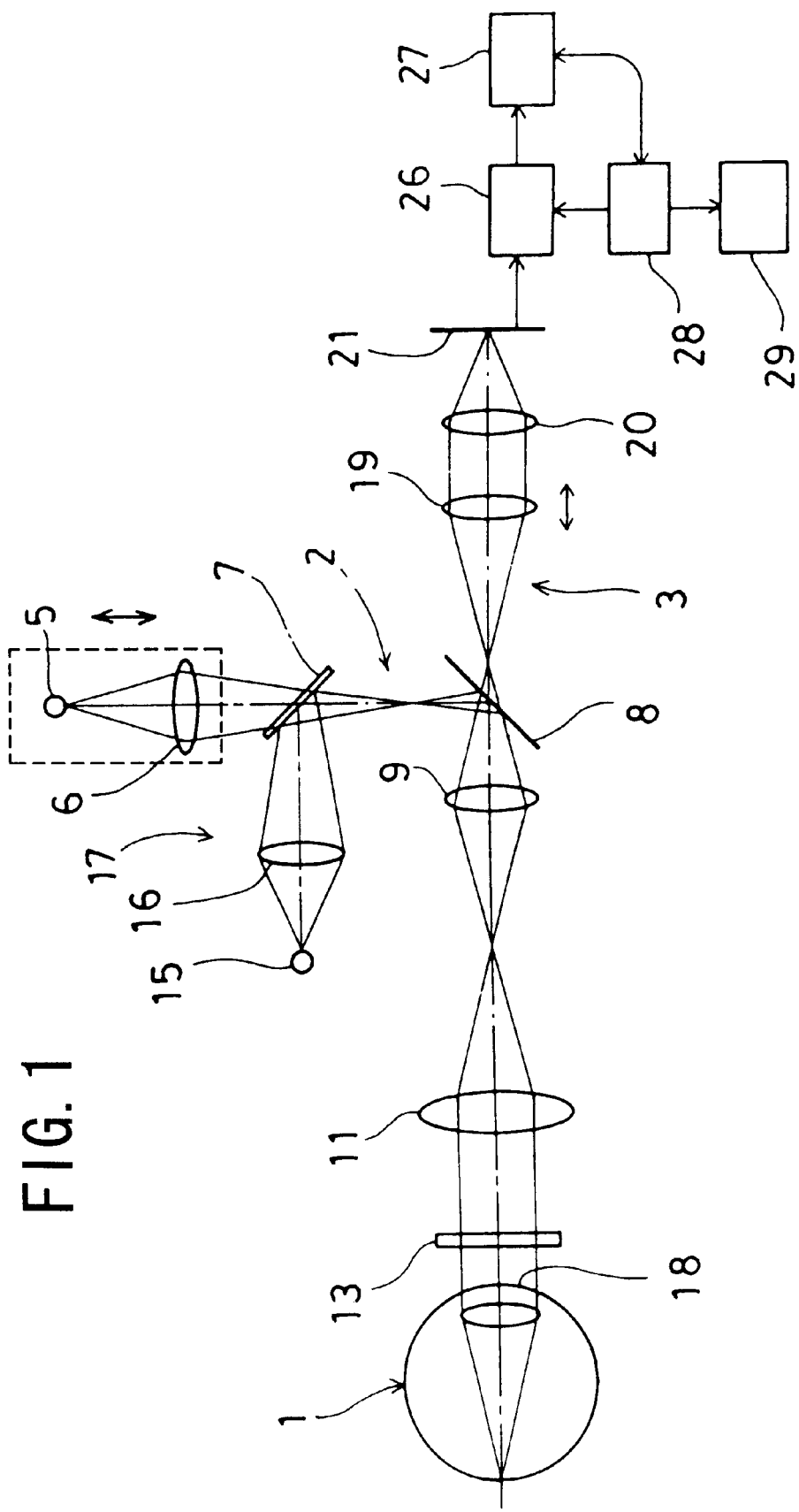
FIG. 1 is a schematical block diagram of an optical system of an embodiment of the present invention.

Description will be given below on embodiments of the present invention referring to the drawings.

Description will be given now on an optical system of an embodiment of the present invention referring to FIG. 1.

In the figure, reference numeral 1 denotes an eye under testing, reference numeral 2 denotes a projection optical system, and reference numeral 3 denotes a photodetection optical system.

The projection optical system 2 comprises a light source 5, a projection lens 6 for converging a projected light beam emitted from the light source 5, a half-mirror 7 arranged on an optical axis of the projection lens 6, a polarization beam splitter 8 for reflecting the projected light beam passing through the half-mirror 7 and for projecting a linearly polarized light component (an S linearly polarized light) of a first polarized direction toward the eye under testing 1, a relay lens 9 arranged on a projection optical axis of the polarization beam splitter 8 from the direction of the polarization beam splitter 8, an objective lens 11, and a ¼ wave plate 13. Further, a fixed target system 17 comprising a fixed target 15 and a condenser lens 16 facing toward the half-mirror 7 is disposed. The light source 5 and the fixed target 15 are at positions to conjugate to the fundus of the eye 1 under testing. As to be described later, each of the light source 5 and the fixed target 15 forms an image on the fundus of the eye. The light source 5 and the projection lens 6 are integrally designed and can be moved along the optical axis in association with the movement of a focusing lens 19 as to be described later.

In common with the projection optical system 2, the photodetection optical system 3 shares the polarization beam splitter 8, the relay lens 9 disposed on the optical axis of the projection light projected from the polarization beam splitter 8, the objective lens 11 and the ¼ wave plate 13.

On the optical axis of the reflected light passing through the polarization beam splitter 8, there are provided the focusing lens 19 and an image forming lens 20. The focusing lens 19 can be moved along the optical axis of the reflected light. The image forming lens 20 forms the reflected light beam as an image on a photoelectric detector 21 arranged at a position conjugate to the fundus of the eye 1 under testing.

A photodetection signal from the photoelectric detector 21 is stored in a storage unit 27 via a signal processing unit 26. In the storage unit 27, targets for a visual acuity test, e.g. Landolt's rings of different size, are stored as a plurality of image data. Writing of the data to the storage unit 27 from the signal processing unit 26 is controlled by a control unit 28. The control unit 28 comprises a simulation image calculating unit and a visual acuity calculating unit. Based on the data stored in the storage unit 27, calculation is made as required, and the result of the calculation is displayed on a display unit 29.

It may be designed in such manner that a separate optical system is provided, and the image data of the target for the visual acuity test may be obtained by forming an image of the target for the visual acuity test on the photoelectric detector 21 by this optical system.

Description will be given below on an operation of the optical system.

A subject person under testing is instructed to gaze at the fixed target 15, and a projection light beam is projected from the projection optical system 2. A visible light is used for the fixed target 15, and an infrared light is used for the projection light beam.

The projected light beam (infrared light) from the light source 5 passes through the projection lens 6 and the half-mirror 7 and reaches the polarization beam splitter 8. An S linearly polarized light component is reflected by the polarization beam splitter 8, and the light component passes through the relay lens 9 and is projected to the fundus of the eye 1 under testing via the ¼ wave plate 13 by the objective lens 11, and a primary index image is formed as a point image.

When the S linearly polarized light passes through the ¼ wave plate 13, it is turned to a right circularly polarized light. The projected light beam is reflected at the fundus of the eye 1 under testing. When the reflected light beam is reflected at the fundus of the eye, it is turned to a left circularly polarized light. Further, when the reflection light beam passes through the ¼ wave plate 13, it is turned to a P linearly polarized light, which has a direction of polarization deviated by an angle of 90° from that of the S linearly polarized light.

The P linearly polarized light is guided toward the polarization beam splitter 8 via the objective lens 11 and the relay lens 9. The polarization beam splitter 8 reflects the S linearly polarized light and allows the P linearly polarized light to pass. Thus, the reflected light beam passes through the polarization beam splitter 8, and a secondary index image is formed on the photoelectric detector 21 by the focusing lens 19 and the image forming lens 20.

A light amount intensity distribution of the secondary index image received at the photoelectric detector 21 reflects an eye's optical characteristic of the eye 1 under testing. By detecting a photodetection status of the photoelectric detector 21, it is possible to measure the eye's optical characteristic.

Next, not all of the projected light beams projected to the fundus of the eye 1 under testing is necessarily reflected on the fundus of the eye 1 under testing. A part of the beam enters from the surface of the fundus into a superficial layer, and scattering reflection, i.e. the so-called bleeding reflection, (hereinafter referred as "scattering reflection") occurs. When the scattering reflection light is received at the photoelectric detector 21 together with the reflection light beam, it is turned to a noise in the light amount intensity distribution of the secondary index image, and the accurate eye's optical characteristic of the ocular optical system cannot be measured.

A polarizing state of the light beam from the scattering reflection is in random state. For this reason, when the light passes through the ¼ wave plate 13 and is turned to a linearly polarized light, only a limited part of the light components matches with the P linearly polarized light. Therefore, almost all of the scattering reflection light components are absorbed by the polarization beam splitter 8, and the light received by the photoelectric detector 21 is the projected reflection light beam, from which scattering reflection light component has been substantially removed. By using the ¼ wave plate 13 as a component element of the projection optical system 2 and the photodetection optical system 3, it is possible to measure the accurate eye's optical characteristic of the ocular optical system.

Based on a photodetection signal from the photoelectric detector 21, the control unit 28 calculates the eye's optical characteristic. From the eye's optical characteristic thus obtained and from the target stored in the storage unit 27, an image can be simulated, which may be formed when the target image is projected to the fundus of the eye under testing, and the image obtained by simulation is stored in the storage unit 27. From this stored image, the control unit 28 calculates a profile 33 (light amount intensity distribution characteristic value) (to be described later) along a meridian direction (target gap direction 32). From the profile 33, the accurate visual acuity value is calculated. The result of the calculation is displayed on the display unit 29.

Figure 2:
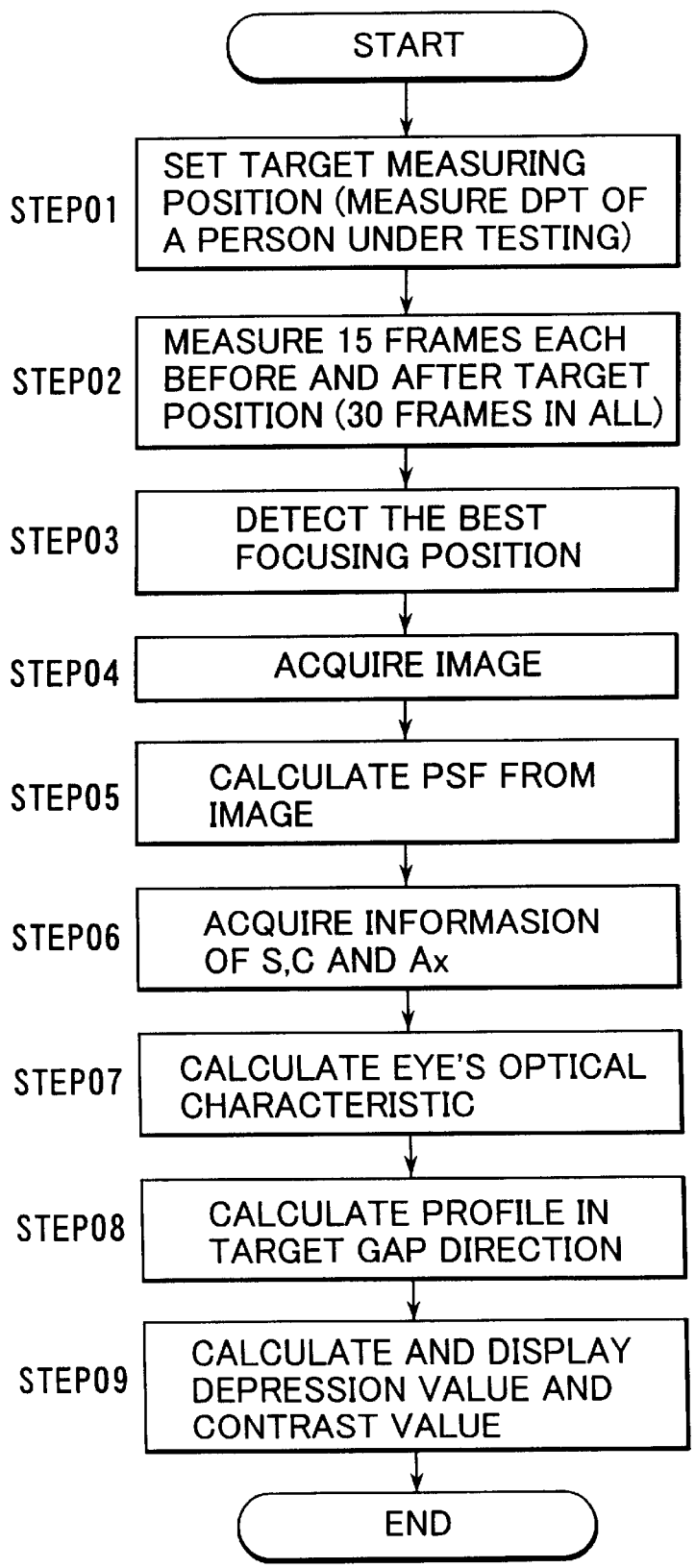
FIG. 2 is a flow chart showing an operation of the embodiment of the present invention.

Description will be given now on an acquisition of the simulation image, and further, on the profile 33 and the calculation of the visual acuity value referring to FIG. 2.

(Step01) While the subject person under testing is instructed to gaze at the fixed target 15, the focusing lens 19 is moved. In association with the movement of the focusing lens 19, the light source 5 and the projection lens 6 are integrally moved. Rough focusing is performed, and a target measuring position corresponding to an ocular refractive power of the eye under testing is set. For this setting, the following methods may be used: a method to perform the setting based on the result of the measurement by an objective refractometer measured in advance, or a method to observe a target image displayed on a monitor based on a signal from the photoelectric detector 21 and to perform focusing so that the target image is roughly focused.

(Step02) Under this condition, using the position set in Step01 as the center, the focusing lens 19 is moved by a predetermined amount of step before and after this position. In association with the movement of the focusing lens 19, the light source 5 and the projection lens 6 are integrally moved. By changing the focusing status on the photoelectric detector 21, an image signal obtained at the photoelectric detector 21 at each step is stored in the storage unit 27 (e.g. frame memory). The image signals to be stored are set, for instance, to signals for 30 frames including the target position (target focusing position).

(Step03) The control unit 28 compares a large number of image data stored in the storage unit 27. If the eye under testing has astigmatism, there are two focusing positions at a front side focal line position and at a rear side focal line position. The data of focusing status such as the positions of the focusing lens 19 at focusing at the front side focal line position or at the rear side focal line position are acquired.

(Step04) The control unit 28 selects two image data at the front side focal line position and the rear side focal line position of the eye under testing. In this case, the index image is focused only in a predetermined meridian direction at the front side focal line position and the rear side focal line position. These are formed as slit-like images different from each other in directions. Thus, the two image data at the front side focal line position and the rear side focal line position are judged and selected according to whether a short side direction of the slit-like image is focused at the most or not.

(Step05) Based on the two image data at the front side focal line position and at the rear side focal line position selected in Step04, the light amount intensity distribution at each position is calculated at the control unit 28. Further, from the light amount intensity distribution at each position, a 2-demensional light amount intensity distribution (PSF: spread function) is calculated.

Referring to FIG. 3, brief description is given now on the 2-dimensional light amount intensity distribution.

Figure 3A:
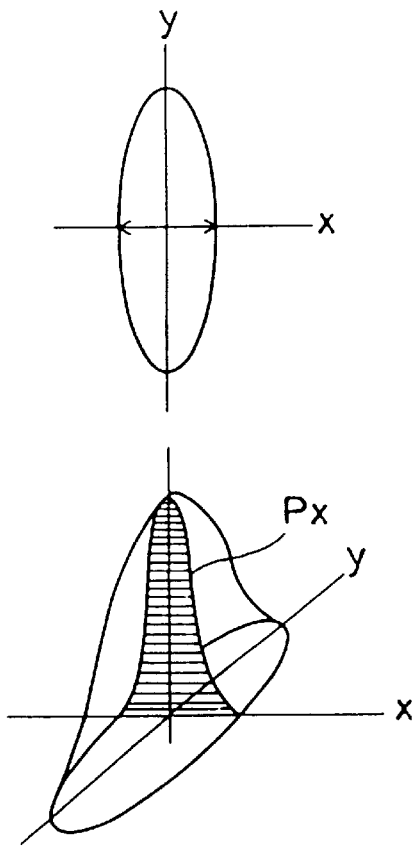
FIG. 3(A) represents diagrams showing a light amount intensity distribution at a rear side focal line position.
Figure 3B:
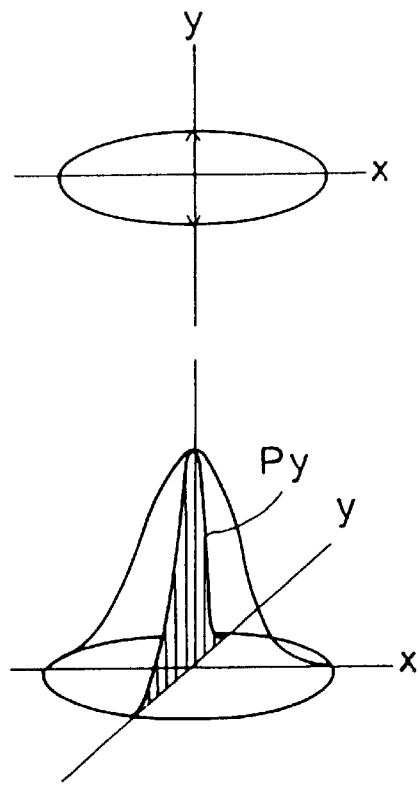
FIG. 3(B) represents diagrams showing a light amount intensity distribution at a front side focal line position.

FIG. 3(A) shows the light amount intensity distribution at the rear side focal line position, and FIG. 3(B) represents the light amount intensity distribution at the front side focal line position.

In the light amount intensity distribution at the rear side focal line position shown in FIG. 3(A), Px, i.e. a cross-section in X direction, shows the light amount intensity distribution in a direction where the light beam is most densely converged at the rear side focal line position.

Similarly, in the light amount intensity distribution at the front side focal line position shown in FIG. 3(B), Py, i.e. a cross-section in Y direction, represents the light amount intensity distribution where the light beam is most densely converged at the front side focal line position.

Figure 4A:
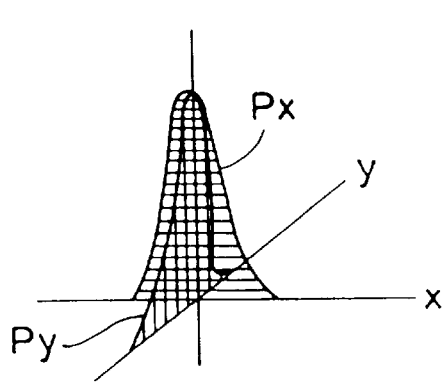
FIG. 4(A) shows the light amount intensity distribution at the rear side focal line position.
Figure 4B:
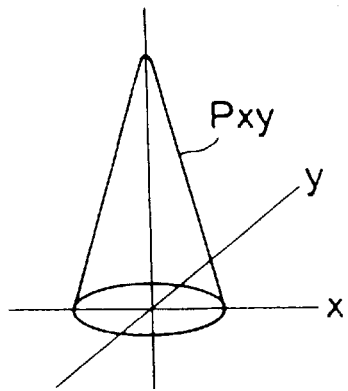
FIG. 4(B) represents a diagram of a 2-dimensional light amount intensity distribution obtained from the light amount intensity distribution at the front side focal line position.

By elliptical approximation at a light amount intensity I (i), the 2-dimensional light amount intensity distribution is given as shown in FIG. 4(A) and FIG. 4(B). For instance, in FIG. 4(B), the 2-dimentional light amount intensity distribution is calculated as Pxy.

(Step06) Information data S, C, and Ax (a spherical degree, an astigmatic degree and an astigmatic axis) of the eye under testing are obtained by the calculation based on factors such as the position data of the focusing lens 19, the directions of the slit images at the front side focal line position and at the rear side focal line position, and at the 2-dimentional light amount intensity distribution Pxy.

A difference in the positions of the focusing lens 19 at the front side focal line position and at the rear side focal line position corresponds to the astigmatic degree S, and the position of the focusing lens 19 at the rear side focal line position corresponds to the spherical degree S. The astigmatic axis Ax can be obtained from the direction of the slit image.

(Step07) As shown in Step05, the above value Pxy is obtained from the light amount intensity distribution at the rear side focal line position and from the light amount intensity distribution at the front side focal line position. The value Pxy is obtained when the projection light beam passes twice through the ocular optical system of the eye 1 under testing. Thus, the following relationship exists between the value Pxy and the spread function (PSF) P'xy of the ocular optical system of the eye 1 under testing:

$$Pxy=(P'xy)^2$$

Therefore, P'xy=√(Pxy). Accordingly, by obtaining the value of Pxy, it is possible to obtain the spread function (PSF) P'xy of the ocular optical system of the eye 1 under testing.

Figure 5:
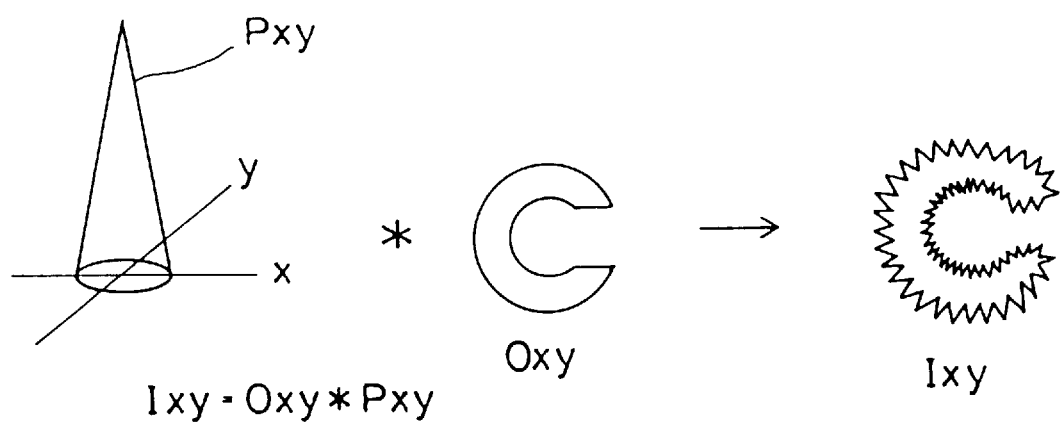
FIG. 5 shows drawings to explain a target for a visual acuity test and a calculated image.

As described above, the image Ixy can be obtained by performing superimposition and integration (convolution integration) of the obtained value Pxy with the target Oxy for visual acuity test such as Landolt's ring as shown in FIG. 5. The target Oxy for visual acuity test is stored as an image data in advance in the storage unit 27. The image Ixy represents an image of the fundus of the eye under testing as obtained when the eye 1 under testing is corrected by a spectacle lens, which combines a spherical lens of refractive power-S diopter with a cylindrical lens of refractive power-diopter. In FIG. 5, notches on the peripheral portion of the image Ixy indicate that the image is blurred.

Here, when Fourier transform FT and inverse Fourier transform IFT are performed:

pxy=FT (Pxy)

oxy=FT (Oxy)

ixy=FT (Ixy)

Therefore, the image Ixy can also be obtained from:

ixy=pxy×oxy

Ixy=IFT (ixy)

Figure 6:
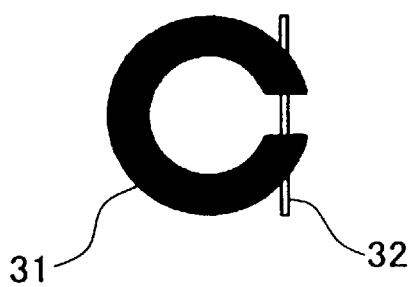
FIG. 6 is a drawing to explain a Landolt's ring target and a target gap direction.
Figure 7:
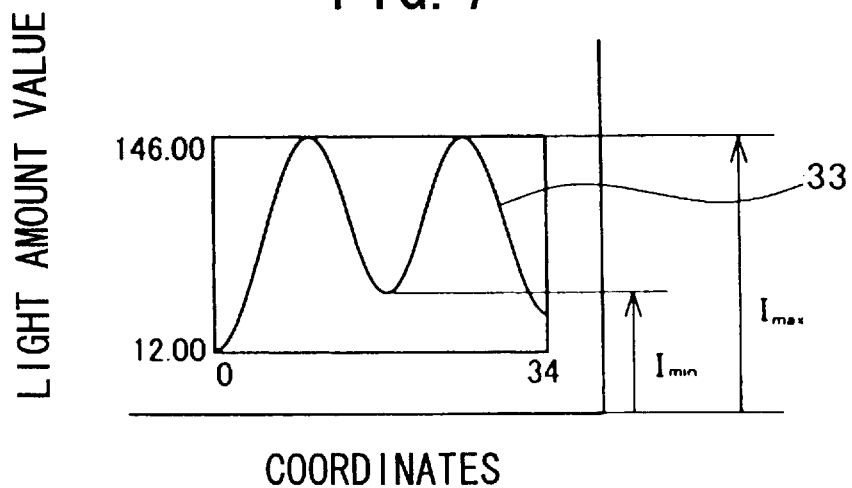
FIG. 7 is a diagram to explain a profile of a light amount intensity distribution in the target gap direction.

(Step08) The image 31 obtained in the above steps is turned to an image as shown in FIG. 6. The profile 33 in a direction traversing the gap (lacked portion of Landolt's ring) of the image 31 is calculated. FIG. 7 is a graphic representation of the profile 33 thus calculated. The profile 33 can be calculated with respect to each target for visual acuity test corresponding to each visual acuity value.

(Step09) Based on each of the values of the profile 33, a depression value and a contrast value can be calculated at the control unit 28.

It is supposed here that the maximum value of the profile 33 is Imax and the minimum value of the profile 33 is Imin. Then, $$\text{Depression value (\%)}=(I\text{max}-I\text{min})\times 100/I\text{max} \quad (1)$$

According to the criterion of Lord Rayleigh, if the depression value is a value of more than 26 (%), the gap is resolvable. That is, when the subject person under testing actually gazes at Landolt's ring, the eye under testing can discriminate the gap of Landolt's ring. In this case, $I\text{min}/I\text{max}=0.74$.

Next, the contrast value is obtained.

$$\text{Contrast value (\%)}=(I\text{max}-I\text{min})\times 100/(I\text{max}+I\text{min})=(1-I\text{min}/I\text{max})\times 100/(1+I\text{min}/I\text{max}) \quad (2)$$

If Imin/Imax=0.74 is substituted, Contrast value=14.9 (%) Thus, the resolvable criterion of the contrast value is about 15 (%). As each of the criterion described above, other values obtained by an experiment may be used. Or, for instance, other criterion may be determined so that coordination is attained with a subjective visual acuity.

As it is evident from the figure, two values are obtained for Imax. One of the values of Imax may be used, or the average value may be used.

The simulation image and the profile 33, etc. thus calculated are shown in contrast as shown in FIG. 8.

In FIG. 8, the image Ixy of the simulation image of the target for visual acuity test corresponding to each visual acuity value (V.A.) is given in the row (A). The profile 33 of the image Ixy corresponding to each of the visual acuity values (V.A.) is given in the row (B). In the row (C), a depression value-visual acuity curve and a contrast value-visual acuity curve are shown. Although it is not shown clearly in the figure, the image Ixy in the row (A) has the contour blurred when the visual acuity value is increased.

As shown in FIG. 8, the image Ixy (see the row (A) in FIG. 8) of the simulation image for the target for visual acuity test corresponding to each of the visual acuity values (V.A.) and the profile 33 of the image Ixy corresponding to each of the visual acuity values (V.A.) are obtained. Further, the maximum value and the minimum value of the profile 33 are obtained. Based on the maximum value and the minimum value, the depression value and the contrast value of each visual acuity are calculated from the equations (1) and (2). Then, by interpolating the results of calculation with a regression curve (e.g. polynomial of degree three), the depression value and the contrast value of the visual acuity values other than the target for visual acuity test used for simulation can be estimated. In FIG. 8, if the original image of the target for visual acuity test stored in the storage unit 27 is displayed with the image Ixy, each of the images can be compared, and this increases visual effect.

As described above, a curve interpolated by the calculation by the control unit 28 is obtained. The curves obtained by the interpolation are shown in the row (C) of FIG. 8. A diagram relating to the depression value (depression value-visual acuity curve) is shown on the left side and a diagram relating to the contrast value (contrast value-visual acuity curve) is shown on the right side.

The depression value and the contrast value are represented on the axis of ordinate, and logarithm of the visual acuity value is shown on the axis of abscissa.

As described above, the target for visual acuity test can be identified in case of the depression value of 16 (%) and the contrast value of 15 (%). Thus, the visual acuity value of the eye under testing can be obtained from the measurement data by finding 26 (%) on the visual acuity value of the depression value-visual acuity curve and 15 (%) on the contrast value-visual acuity curve.

According to the diagram of FIG. 8 (C), 26 (%) on the depression value-visual acuity curve is log V.A.=0.272. Therefore, the visual acuity value (V.A.) is 1.87.

Also, 15 (%) on the contrast value-visual acuity curve is log V.A.=0.262. Therefore, the visual acuity value is 1.83.

That is, from 26 (%) on the depression value-visual acuity curve and 15 (%) on the contrast value-visual acuity curve, the control unit 28 can calculate the visual acuity value of the eye under testing.

As described above, from the depression value-visual acuity curve or from the contrast value-visual acuity curve, the visual acuity value of the eye under testing can be quantitatively and objectively determined. Further, an attainable visual acuity value in the corrected condition can be estimated. The tester can explicitly identify the optical characteristic of the eye under testing from the form and the features of the depression value-visual acuity curve and the contrast value-visual acuity curve.

In the target for visual acuity test described above, Landolt's ring is used. It is also possible to use the original target for visual acuity test, which is designed in such manner that the depression value is more clearly defined. Various types of targets for visual acuity test such as log MAR chart can be used. The contrast value is not limited only to the two values of white/black. By using gray chart, the visual acuity value can be estimated more precisely.

In the above embodiment, Landolt's ring for visual acuity test having one gap is used as the fixed target 15, while a target having a plurality of gaps may be used to increase the measurement accuracy.

FIG. 9 shows an annular target 34, which has a gap Gh in an angle of 0° direction, a gap Gv in an angle of 90° direction, a gap Gru in an angle of 45° direction, and a gap Grd in an angle of 135° direction.

A predetermined number of the targets 34 with size corresponding to the visual acuity values (symmetrical and different in size) are prepared. The simulation image is calculated by convolution integration of the target 34 corresponding to each of the visual acuity values with the eye's optical characteristic (corresponding to the row (A) in FIG. 8). Further, on the simulation image thus obtained, for each of the gaps Gh, Gv, Gru and Grd, the profiles are obtained in the meridian direction perpendicular to the direction of each gap in the target, i.e. the target gap directions of 35H, 35V, 35RU and 35RD (see FIG. 10).

For each of the profiles of the target gap directions 35H, 35V, 35RU and 35RD, the maximum value Imax and the minimum value Imin are obtained. From the maximum value Imax and the minimum value Imin, the depression value and the contrast value as described above are obtained.

Interpolation is performed between the depression values obtained on each simulation image of the target 34 or between the depression values obtained by calculation with a regressive curve. Also, interpolation is performed between the contrast values obtained on each simulation image of target 34 or the contrast values obtained by calculation with a regressive curve. As a result, the depression value—visual acuity curve or the contrast value-visual acuity curve for each of the profiles of target gap directions of 35H, 35V, 35RU and 35RD are obtained.

FIG. 11 is a diagram showing the contrast value-visual acuity curves 36H, 36V, 36RU and 36RD for each of the target gap directions of 35H, 35V, 35RU and 35RD.

As described above, regarding the contrast value, the resolvable criterion is 15 (%). When log V.A. at 15 (%) is obtained on the contrast value-visual acuity curves 36H, 36V, 36RU and 36RD in FIG. 11:

log H=0.258
log V=0.260
log RU=0.196
log RD=0.125

Further, in average value: $\log_{Avg}$=0.210. In this case, the visual acuity values (V.A.) are:

H: 1.81
V: 1.82
RU: 1.57
RD: 1.33

The average visual acuity value is 1.62.

As shown in FIG. 9, the target 34 having a plurality of gaps is used, and the average visual acuity value is obtained based on a plurality of profiles different in the meridian direction. As a result, it is possible to estimate the visual acuity value with high accuracy.

It is needless to say that the same effect can be attained when the stored image of target is rotated adequately by using the Landolt's ring or a target having a gap in one direction. From each of the rotated target images and the eye's optical characteristic, the simulation image is calculated, and the profile may be obtained for a plurality of meridian directions for the simulation image. The angle of the meridian direction is not limited to the angle as given above, and it may be at any angle in the range of 0°–180°.

Next, description will be given on another embodiment referring to FIG. 12.

In this another embodiment, the image Ixy of the target for visual acuity test corresponding to each of the visual acuity values (V.A.) in the row (A) in FIG. 8 is obtained by a different method. From the image Ixy thus obtained, a profile 33 of the image Ixy corresponding to each of the visual acuity value V.A. is obtained. Further, the depression value-visual acuity curve and the contrast value-visual acuity curve in the row (C) of FIG. 8 are obtained by the same procedure as in the first embodiment described above.

Figure 12:
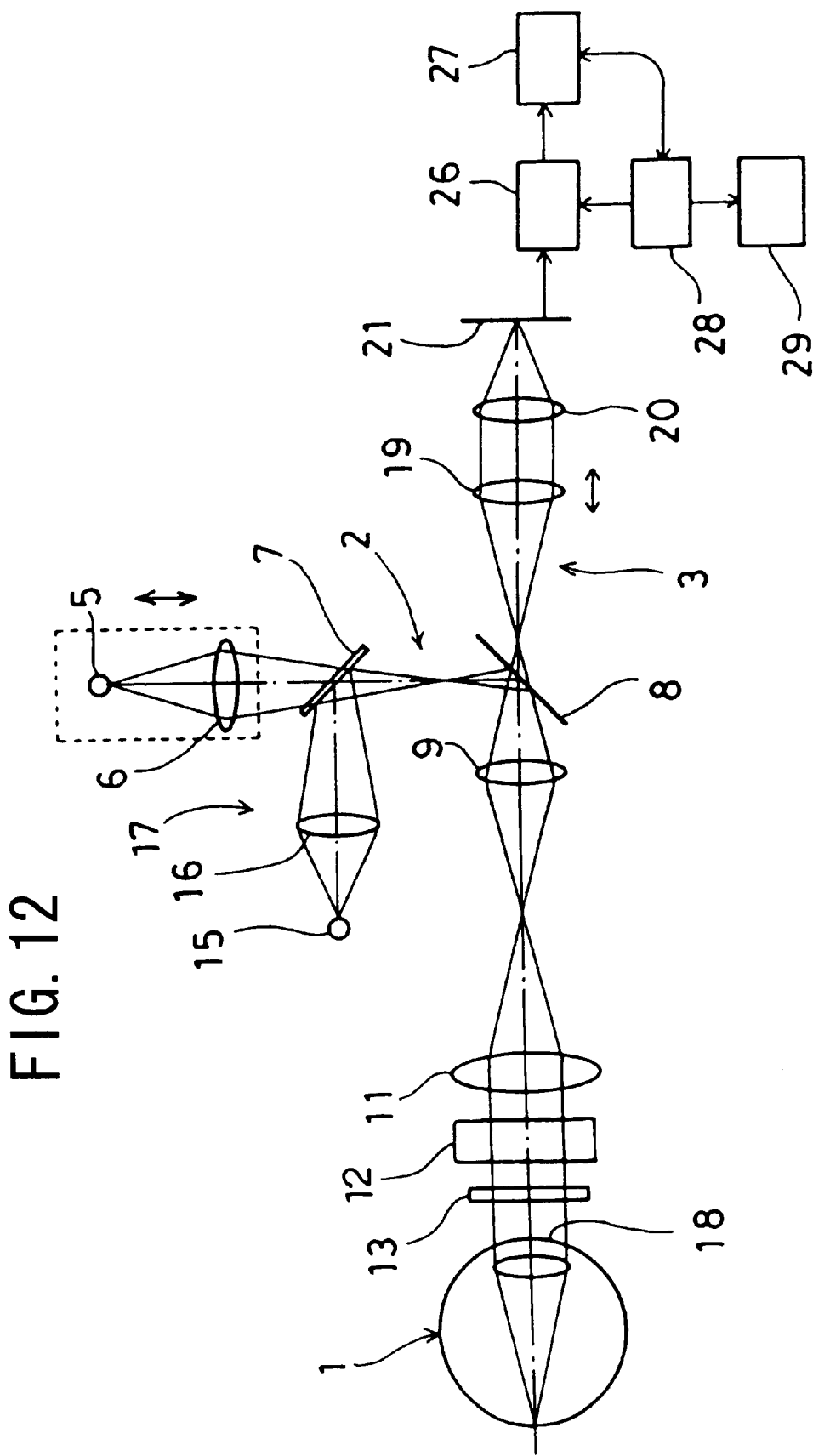
FIG. 12 is a schematical block diagram of an optical system of another embodiment of the present invention.

FIG. 12 shows the optical system of this second embodiment. In the optical system of this embodiment, a correction optical system 12 is added to the optical system of the first embodiment given in FIG. 1, and the ¼ wave plate 13 is removably arranged with respect to the optical axis. The other components are the same, and detailed description is not given here.

The correction optical system 12 comprises a spherical lens, and the spherical lens is arranged between the objective lens 11 and the eye 1 under testing. As described above, the ¼ wave plate 13 is removably arranged with respect to the optical axis.

Description will be given below on an operation of this second embodiment.

The focusing lens 19 is adjusted to a reference position. The subject person is instructed to gaze at the fixed target 15 with the eye 1 under testing, and the visual acuity of the eye 1 under testing is corrected by the correction optical system 12.

After correcting the ocular refractive power, while the eye 1 under testing is gazing at the fixed target 15, the projection light beam is projected to the fundus of the eye under testing by the projection optical system 2. A visible light is used for the fixed target 15, and an infrared light is used for the projection light beam.

First, description will be given on the condition where the ¼ wave plate 13 is inserted in the optical path.

The projection light beam (infrared light) from the light source 5 passes through the projection lens 6 and the half-mirror 7 and reaches the polarization beam splitter 8. The S linearly polarized light component is reflected by the polarization beam splitter 8. Then, the S linearly polarized light component passes through the relay lens 9 and is projected to the fundus of the eye 1 under testing via the ¼ wave plate 13 by the objective lens 11 the correction optical system 12, and the primary index image is formed on the fundus of the eye.

When the S linearly polarized light passes through the ¼ wave plate 13, the S linearly polarized light is turned to a right circularly polarized light. At the fundus of the eye 1 under testing, the projection light beam is totally reflected. The totally reflected light beam is turned to a left circularly polarized light when the totally reflected light beam is reflected by the fundus of the eye. Further, when the totally reflected light beam passes through the ¼ wave plate 13, the S linearly polarized light is turned to a P linearly polarized light, which has a direction of polarization deviated by an angle of 90° from that of the S linearly polarized light.

The P linearly polarized light is guided toward the polarization beam splitter 8 by the correction optical system 12, the objective lens 11, and the relay lens 9. The polarization beam splitter 8 reflects the S linearly polarized light, while the polarization beam splitter 8 allows the P linearly polarized light to pass. As a result, the totally reflected light beam passes through the polarization beam splitter 8, and the secondary index image is formed on the photoelectric detector 21 by the focusing lens 19 and the image forming lens 20.

At the fundus of the eye 1 under testing, the total reflection and the scattering reflection occur as described above. When the light beam reflected by the scattering reflection is received at the photoelectric detector 21 together with the totally reflected light beam, the scattering reflection light beam is turned to a noise in the light amount intensity distribution of the secondary target image, and the eye's optical characteristic of ocular optical system cannot be measured accurately.

As described above, the polarizing state of the light beam reflected by the scattering reflection is in a random state. For this reason, when the light beam passes through the ¼ wave plate 13 and is turned to the linearly polarized light, only a limited part of it matches with the P linearly polarized light. All other light components of the scattering reflection light except the beam matching with the P linearly polarized light is reflected by the polarization beam splitter 8. Therefore, the P linearly polarized light component by the scattering reflection light beam has the ratio as small as negligible with respect to the P linearly polarized light component totally reflected at the fundus of the eye 1 under testing.

Therefore, the light beam received by the photoelectric detector 21 is the totally reflected light beam, from which the scattering reflection light component has been substantially removed. By using the ¼ wave plate 13 as a component element of the projection optical system 2 and the photo-detection optical system 3, it is possible to measure accurate the eye's optical characteristic of the ocular optical system.

The light amount intensity distribution of the secondary index image received by the photoelectric detector 21 reflects the eye's optical characteristic of the eye 1 under testing itself. By detecting the photodetection state of the photoelectric detector 21, it is possible to measure the eye's optical characteristic.

Next, description will be given on the condition where the ¼ wave plate 13 is withdrawn from the optical path.

Because the ¼ wave plate 13 is withdrawn, the polarizing state of the totally reflected light beam from the fundus of the eye remains in the state of the S linearly polarized light, and the reflected light beam is totally reflected by the polarization beam splitter 8. Therefore, only the P linearly polarized light component of the scattering reflection light beam reflected at the fundus of the eye by the scattering reflection passes through the polarization beam splitter 8. A secondary index image by the scattering reflection light beam is formed on the photoelectric detector 21. The light amount intensity distribution of the secondary index image received by the photoelectric detector 21 is reflecting the fundus optical characteristic of the fundus of the eye and the eye's optical characteristic of the eye 1 under testing.

Based on the photodetection status of the photoelectric detector 21 when the ¼ wave plate 13 is inserted, and also based on the photodetection status of the photoelectric detector 21 when the ¼ wave plate 13 is withdrawn, the fundus optical characteristic can be measured by the procedure as given below.

By inserting or removing the ¼ wave plate 13, it is possible to select whether the reflection light beam projected to the photoelectric detector 21 is the totally reflected light beam totally reflected by the fundus of the eye or the scattering reflection light beam reflected from the fundus of the eye by the scattering reflection. Thus, the ¼ wave plate 13 has the function as light beam switching means.

Figure 13A:
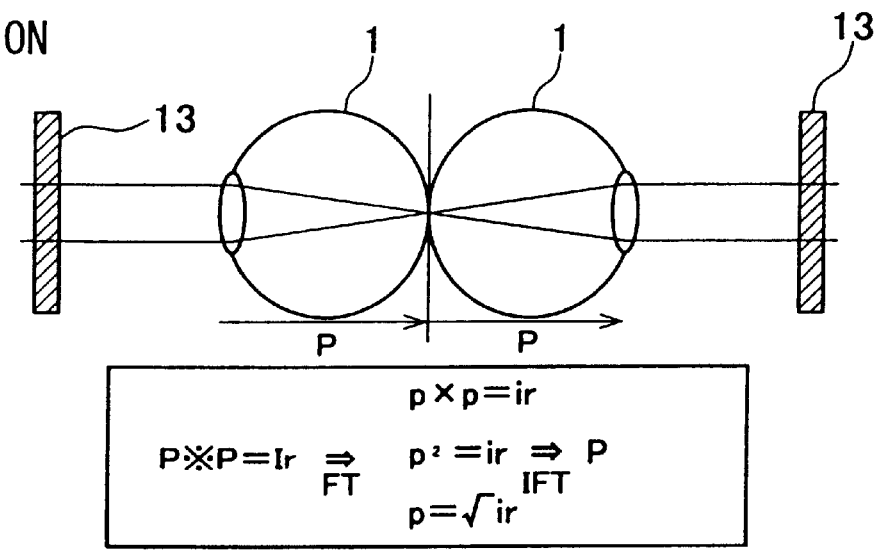
FIG. 13(A) is a drawing to explain a total reflection status at the fundus of an eye under testing.

As shown in the FIG. 13(A), here is a case where the ¼ wave plate 13 is inserted in the optical path, i.e. a case where the scattering reflection light beam is removed. Now, it is supposed that the optical characteristic of ocular optical system of the eye 1 under testing is P, and that the 2-dimensional light amount intensity distribution on the photoelectric detector 21 when the photoelectric detector 21 receives the totally reflected light beam reflected at the fundus of the eye is Ir. Because the totally reflected light beam received at the photoelectric detector 21 passes through the eye 1 under testing twice, the following relationship exists between P and Ir:

$$P \otimes P = Ir$$

where the symbol $\otimes$ means convolution integration.

When Fourier transform is performed on P and Ir respectively,

FT (P)=p

FT (Ir)=ir

Then, it is expressed as:

$$p^2 = ir \tag{3}$$

Figure 13B:
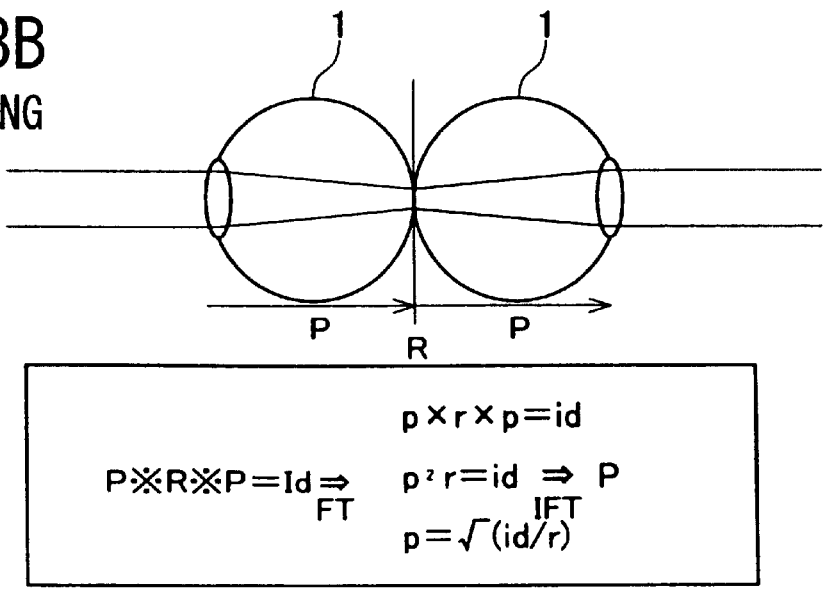
FIG. 13(B) shows a scattering reflection status at the fundus of the eye under testing.

Next, as shown in FIG. 13(B), here is a case where the ¼ wave plate 14 is withdrawn, i.e. a case where the reflection light beam is the light beam by the scattering reflection only. Now, it is supposed that the optical characteristic of the ocular optical system of the eye 1 under testing is P, and that the 2-dimensional light amount intensity distribution on the photoelectric detector 21 when the scattering reflection light beam reflected by the fundus of the eye is received is Id. Because the scattering reflection light beam received at the photoelectric detector 21 passes through the eye 1 under testing twice, and further because the scattering reflection light beam reflects the optical characteristic of the fundus of the eye, the following relationship exists between P and Id:

$$P \otimes R \otimes P = Id$$

When Fourier transform is performed on P, R and Id respectively,

FT (P)=P

FT (R)=r

FT (Id)=id

Then, this is expressed as:

$$p \times r \times p = p^2 \times r = id \tag{4}$$

From the equations (3) and (4), $$r = id/ir$$

Further, when inverse Fourier transform is performed, $$R = IFT(id/ir) \tag{5}$$

That is, $$FT(Ir) = ir$$

$$FT(Id) = id \tag{6}$$

Therefore, the light amount intensity distribution Ir by the totally reflected light beam reflected at the fundus of the eye and the light amount intensity distribution Id by the scatting reflection light beam reflected at the fundus of the eye are respectively measured on the photoelectric detector 21. Then, based on the above equation (3), it is possible to calculate the optical characteristic of the fundus of the eye, which quantitatively indicates deterioration of the image formed by the scattering reflection at the fundus of the eye.

By the procedure as described above, the optical characteristic of the fundus of the eye can be measured, and the simulation image at the fundus of the eye can be calculated by taking the optical characteristic of the fundus of the eye into account.

By adjusting the correction optical system 12 or the focusing lens 19, the target image on the fundus of the eye when a target image is projected on the fundus of the eye under testing under any condition can be simulated by the following procedure:

In this case, when the light amount intensity of the target image formed on the photoelectric detector 21 is measured, the measurement is performed under the condition that the ¼ wave plate 13 is withdrawn and the scattering reflection light beam is received. There is no change on the optical characteristic of the fundus of the eye obtained by the above procedure.

Here, it is supposed that an optical light transfer function of the ocular optical system is Pa, that an optical light transfer function of the fundus of the eye caused by the scattering reflection at the fundus of the eye is R, and that the light amount intensity distribution on the photoelectric detector when the scattering reflection light beam is received is Ia. Then, the following relationship exists:

$$Pa \cdot R \cdot Pa = Ia \quad (7)$$

Fourier transform is performed as described above:

$$FT(Pa) = pa$$

$$FT(R) = r$$

$$FT(Ia) = ia$$

Further, $$Pa^2 \times r = ia$$

Then, $$pa = \sqrt{(ia/r)} \quad (8)$$

When inverse Fourier transform is performed:

$$Pa = IFT(\sqrt{(ia/r)}) \quad (9)$$

If the light amount intensity distribution Ia on the photoelectric detector 21 is measured, it is possible to calculate a light transfer function under any condition based on the value of R calculated as above. By performing convolution integration of Pa thus calculated with the light amount intensity distribution function O of the target actually used, the simulation image of the image I when the target image is projected on the fundus of the eye under testing can be calculated by following equation:

$$I = Pa \cdot O \quad (10)$$

Therefore, by displaying the simulation image on the display unit, it is possible to observe an image at real time, which is actually recognized by the person under testing under any ocular refractive power correction condition and under any focusing condition.

Now, description will be given on the measurement of the eye's optical characteristic of the eye under testing referring to FIG. 14.

(Step01) With the eye 1 under testing gazing at the fixed target 5, the visual acuity of the eye under testing is corrected to correspond to the spherical degree, the astigmatic degree and the astigmatic axis of the eye under testing by the correction optical system 12. For this correction, the following methods may be used: a method to correct based on the result of measurement by an objective refractometer measured in advance, or a method to observe a target image displayed on a monitor based on a signal from the photoelectric detector 21 and to perform correction so that the target image is observed as a point image.

(Step02) The ¼ wave plate 13 is inserted, and the totally reflected light beam at the fundus of the eye is selected.

(Step03) The secondary index image is formed on the photoelectric detector 21 by the totally reflected light beam, and a first light amount intensity distribution Ir is measured from a photodetection signal based on the secondary index image. The first light amount intensity distribution Ir is stored in the storage unit 27.

(Step04) The ¼ wave plate 13 is withdrawn, and the photodetection light beam is turned to the scattering reflection light beam.

(Step05) The secondary index on the photoelectric detector 21 is formed only by the scattering reflection light beam. From the photodetection signal based on the secondary index image, the second light amount intensity distribution Id is measured, and the second light amount intensity distribution is stored in the storage unit 27.

(Step06) At the control unit 28, the fundus optical characteristic R of the eye 1 under testing is calculated from the result of the measurements in Step03 and Step05. The fundus optical characteristic R is stored in the storage unit 27.

(Step07) The ¼ wave plate 13 is withdrawn, and the scattering reflection light beam is selected.

(Step08) The light amount intensity distribution Ia is measured from the photodetection signals based on the index image, which is formed on the photoelectric detector 21. The light amount intensity distribution Ia is stored in the storage unit 27.

(Step09) Because the fundus optical characteristic R is already obtained, the eye's optical characteristic Pa under any focusing condition can be obtained by the equations (7) and (9). Further, by the equation (10), the simulation image is calculated.

(Step 10) Based on the simulation image obtained in Step 09, the profile 33 in a direction of the gap of the target for visual acuity test is calculated.

(Step 11) A depression value, a contrast value, a depression value-visual acuity curve, and a contrast value-visual acuity curve are calculated.

The procedure to obtain the profile 33, the depression value, the contrast value, the depression value-visual acuity curve, and the contrast value-visual acuity curve as well as the procedure to estimate the visual acuity value from the depression value-visual acuity curve and the Contrast value-visual acuity curve are the same as in the embodiment described above, and detailed description is not given here.

The system according to the present invention comprises an index projection system for projecting an index image on a fundus of an eye under testing, a photodetection optical system for guiding the index image toward a photoelectric detector, a simulation image calculating unit for calculating each of images of target images formed when a plurality of target images different in size are respectively projected on the fundus of the eye under testing based on a light amount intensity distribution of the index image detected on the photoelectric detector, and a visual acuity calculating unit for calculating a visual acuity value of the eye under testing, wherein the simulation image calculating unit calculates light amount intensity distributions in each of predetermined meridian directions of the images of the target images, and the visual acuity calculating unit detects a plurality of light amount intensity distribution values based on the light amount intensity distributions and calculates the visual acuity value of the eye under testing based on the plurality of light amount intensity distribution values. Accordingly, there is no need to use the so-called subjective optometric method to measure the visual acuity value based on the response from the person under testing by showing target images for visual acuity test different in size. By simply projecting a predetermined target image to the fundus of the eye and by measuring the light amount intensity distribution of the index image, it is possible to accurately measure the visual acuity value of the eye under testing by arithmetic operation.

What is claimed is:

1. An eye's optical characteristic measuring system, comprising an index projection system for projecting an index image on a fundus of an eye under testing, a photodetection optical system for guiding the index image toward a photoelectric detector, a simulation image calculating unit for calculating each of images of target images formed when a plurality of target images different in size are respectively projected on the fundus of the eye under testing based on a light amount intensity distribution of the index image detected on the photoelectric detector, and a visual acuity calculating unit for calculating a visual acuity value of the eye under testing, wherein said simulation image calculating unit calculates light amount intensity distributions in each of predetermined meridian directions of the images of the target images, and said visual acuity calculating unit detects a plurality of light amount intensity distribution values based on the light amount intensity distributions and calculates the visual acuity value of the eye under testing based on the plurality of light amount intensity distribution values.

2. An eye's optical characteristic measuring system according to claim 1, wherein the light amount intensity distribution characteristic value is detected based on each light amount distribution in a in a plurality of the predetermined meridian directions of the image of each target image, and the visual acuity value of the eye under testing is calculated based on the values of light amount intensity distribution characteristic in said plurality of the predetermined meridian directions.

3. An eye's optical characteristic measuring system according to claim 2, wherein the visual acuity value of the eye under testing is calculated from an average value of the light amount intensity distribution characteristic values obtained in each of the predetermined meridian directions.

4. An eye's optical characteristic measuring system according to claim 2, wherein a light amount intensity distribution characteristic value—visual acuity curve is obtained by interpolating a plurality of light amount intensity distribution characteristic values in the predetermined meridian direction and the visual acuity value of the eye under testing is calculated based on the light amount intensity distribution characteristic value—visual acuity curve.

5. An eye's optical characteristic measuring system according to claim 4, wherein the tight amount intensity distribution characteristic value of the image of the target image is a contrast value.

6. An eye's optical characteristic measuring system according to claim 4, wherein the light amount intensity distribution characteristic value of the image of the target image is a depression value.

7. An eye's optical characteristic measuring system according to claim 4, wherein at least one gap is formed in the target image, and said predetermined meridian direction is a direction to traverse the gap of the image of the target image.

8. An eye's optical characteristic measuring system according to claim 1, wherein a light amount intensity distribution characteristic value—visual acuity curve is obtained by interpolating a plurality of light amount intensity distribution characteristic values in the predetermined meridian direction and the visual acuity value of the eye under testing is calculated based on the light amount intensity distribution characteristic value—visual acuity curve.

9. An eye's optical characteristic measuring system according to one of claims 1 to 8, wherein the light amount intensity distribution characteristic value of the image of the target image is a contrast value.

10. An eye's optical characteristic measuring system according to one of claims 1 to 8, wherein the light amount intensity distribution characteristic value of the image of the target image is a depression value.

11. An eye's optical characteristic measuring system according to one of claims 1 to 8, wherein at least one gap is formed in the target image, and said predetermined meridian direction is a direction to traverse the gap of the image of the target image.

* * * * *